(12) United States Patent
Owens et al.

(10) Patent No.: US 9,008,379 B2
(45) Date of Patent: Apr. 14, 2015

(54) PAY FOR STUDIES SUBMITTED (PASS) METHOD FOR CLINICAL TRIALS

(75) Inventors: Steven F. Owens, Denville, NJ (US); Gudrun Zahlmann, Neumarkt (DE); Patrick K. DeGrouchy, Media, PA (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 1602 days.

(21) Appl. No.: 12/062,148

(22) Filed: Apr. 3, 2008

(65) Prior Publication Data

US 2009/0112619 A1   Apr. 30, 2009

Related U.S. Application Data

(60) Provisional application No. 60/982,780, filed on Oct. 26, 2007.

(51) Int. Cl.
*G06K 9/00* (2006.01)
*G06F 19/00* (2011.01)
*G06Q 50/22* (2012.01)

(52) U.S. Cl.
CPC ............ *G06F 19/363* (2013.01); *G06F 19/321* (2013.01); *G06Q 50/22* (2013.01)

(58) Field of Classification Search
CPC ........................................................ G06K 9/00
USPC ............................................................ 705/2
See application file for complete search history.

(56) References Cited

U.S. PATENT DOCUMENTS

| 5,274,774 | A  | * | 12/1993 | Manber et al. ................ 710/125 |
| 6,519,632 | B1 | * | 2/2003  | Brackett et al. ............... 709/219 |
| 7,047,235 | B2 | * | 5/2006  | Yang et al. .................... 707/661 |
| 7,187,790 | B2 | * | 3/2007  | Sabol et al. .................... 382/128 |
| 7,401,028 | B2 | * | 7/2008  | Deakter ............................ 705/3 |
| 7,860,287 | B2 | * | 12/2010 | Zahlmann et al. ............. 382/128 |
| 8,793,145 | B2 | * | 7/2014  | Kahn et al. ........................ 705/3 |
| 2002/0002474 | A1 | * | 1/2002  | Michelson et al. ................ 705/3 |
| 2002/0091827 | A1 | * | 7/2002  | King et al. ..................... 709/226 |
| 2004/0002925 | A1 | * | 1/2004  | Gordon .......................... 705/401 |
| 2005/0065438 | A1 | * | 3/2005  | Miller ............................ 600/437 |
| 2005/0251011 | A1 | * | 11/2005 | Zahlmann et al. ............. 600/407 |
| 2006/0247955 | A1 | * | 11/2006 | Humphrey ........................ 705/5 |
| 2007/0100885 | A1 |   | 5/2007  | Sumino et al. |
| 2007/0150223 | A1 |   | 6/2007  | Abraham-Fuchs |
| 2007/0255587 | A1 |   | 11/2007 | Chien et al. |
| 2008/0249807 | A1 | * | 10/2008 | Niwa et al. ........................ 705/3 |

* cited by examiner

*Primary Examiner* — Michael Fuelling
(74) *Attorney, Agent, or Firm* — Peter Kendall (57) ABSTRACT

A system and method is disclosed for facilitating the acquisition of medical images used as part of a clinical trials process by requiring Imaging Centers to compete with each other to supply the images. Agreements between the Sponsor and a plurality of Imaging Centers stipulate that the Sponsor is only required to accept a certain total number of medical images and is free to reject any medical images that either do not comply with the protocol, or which exceed the total number of medical images required for the study. This motivates the Imaging Centers to quickly obtain and transmit to the Sponsor high quality medical images that meet the basic requirements outlined in the clinical study protocol, since images are accepted and compensated for by the Sponsor on a first-come, first-served basis. A system for implementing this method is also disclosed.

20 Claims, 5 Drawing Sheets

PAY FOR STUDIES SUBMITTED (PASS) METHOD FOR CLINICAL TRIALS

CROSS-REFERENCE TO RELATED APPLICATIONS

This is a U.S. non-provisional patent application of U.S. provisional patent application Ser. No. 60/982,780, filed Oct. 26, 2007, by Steven Owens et al., the entirety of which application is incorporated herein by reference.

FIELD OF THE DISCLOSURE

The disclosure relates to a system and method for enhancing the acquisition and review process for medical images in the context of a clinical trials program, and more particularly to a system and method for introducing a competitive element for obtaining medical images as part of a clinical trials program.

BACKGROUND OF THE DISCLOSURE

In the course of developing new drugs, manufacturers must collect significant pre-clinical and clinical data as part of the clinical trials process to prove the safety and effectiveness of new compounds for specific clinical indications. Recent trends include the gathering of medical images to provide additional supporting evidence, or to provide an additional safety measure during the clinical trials process.

Figure 1:
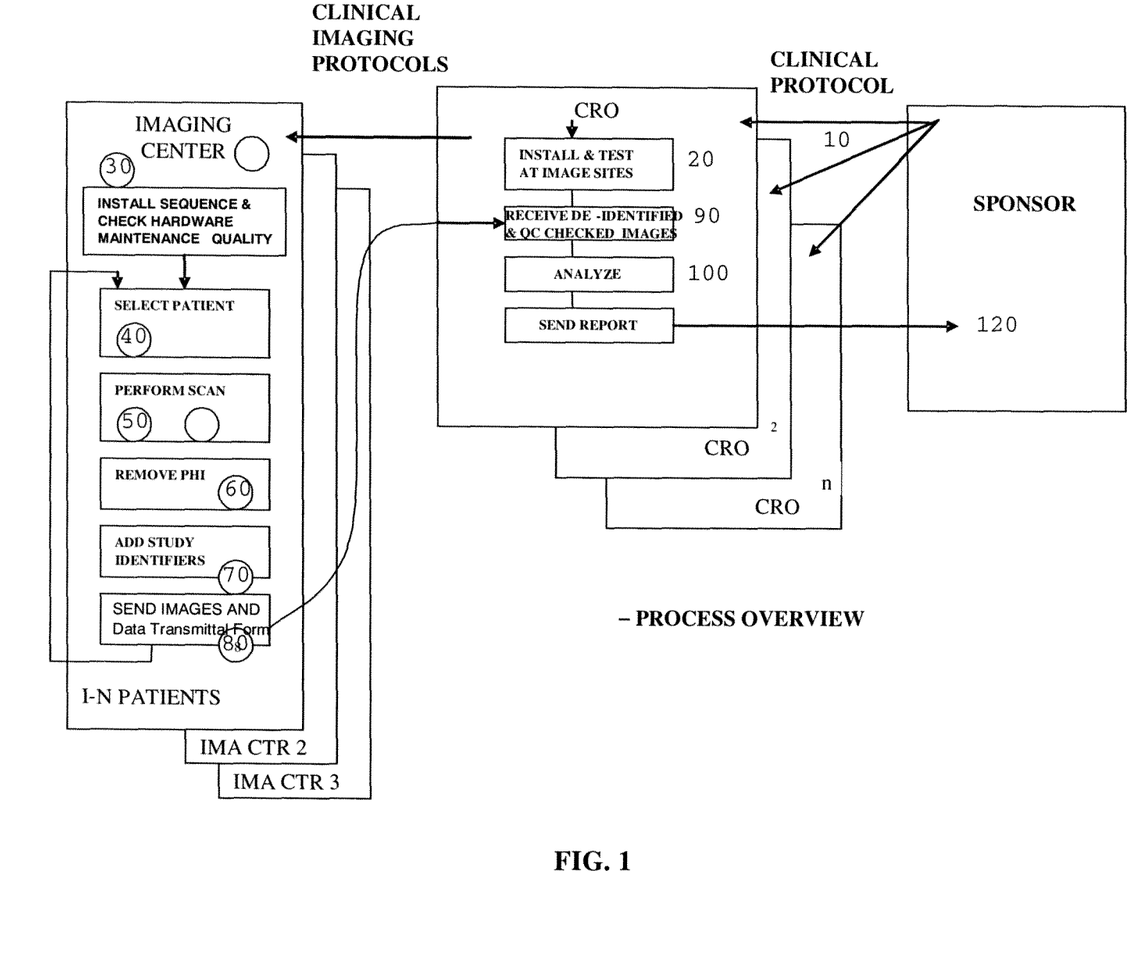
FIG. 1 illustrates a conventional method of obtaining, transmitting and analyzing medical images as part of a clinical trial program.

Typically a manufacturer or Sponsor of a clinical trial will establish a contract with one or more imaging centers to perform the image acquisition on the patients that are part of the trial. In addition, the Sponsor may contract with one or more Clinical Research Organizations (CROs) to gather and evaluate the images acquired by the imaging centers, and to compose statements that prove or disprove findings based on the image data acquired and a clinical protocol. The current process is shown in FIG. 1. As can be seen, at step 10 the Sponsor provides a Clinical Protocol to one or more CRO's. (Although the description will proceed by referring to a single CRO, it will be appreciated that there may be more than one CRO involved in a particular trial). The Clinical Protocol is an action plan or guideline that must be followed during the course of the study. Examples of such guidelines include a description of what will be studied and how, criteria for patients who may enter the study, and specifically what medical images will be acquired for each entered patient.

The Sponsor establishes a business contract with a CRO to perform the clinical protocol. This agreement identifies the clinical protocol to be performed as well as the particular Imaging Centers that will participate in the study. In turn, the CRO creates a clinical imaging protocol for the Imaging Centers to use. The CRO performs initial site readiness and qualification testing 30 at the Imaging Centers, and also establishes the imaging protocols (magnetic resonance imaging (MRI) or computed tomography (CT) parameters, for example) at the Imaging Centers.

As part of the above process, the Sponsor may establish a business contract with the one or more of Imaging Centers who will provide image acquisition services during the trial. The agreement typically specifies how many patients are needed in the study and how many data sets the Imaging Center must deliver. It also stipulates when the images must be sent to the CRO. Before sending the images, the Imaging Center must de-identify the data and add study identifiers before sending the data. As part of the image acquisition services, at 30, the Imaging Centers may install necessary hardware and software to support the imaging protocols. The Imaging Centers may select one or more patients for scanning 40. Once the patients are scanned 50, the Imaging Center may remove any patient-personal identification data from the images 60. Study identifiers are then added to the images 70. At 80, the images may be sent to the CRO, which receives the de-identified images at 90, analyzes them in accordance with the Clinical Protocol at 100, then collects the analyses together along with other information to form the final report at 110. The report is then sent to the Sponsor at 120. As noted, this process can occur using multiple CRO's and multiple Imaging Centers.

Typically the Imaging Center are required to send the images to the CRO within two weeks of having acquired the image. In the ideal case, the Imaging Center ships the imaging study immediately (within 24 hours) to the CRO for evaluation. Once a sufficient number of images have been received, the CRO then analyzes the images and draws conclusions based on the study protocol. These conclusions are then communicated to the Sponsor as part of their final report.

In practice, however, the Imaging Centers commonly make errors in the image data acquisition. This is primarily due to the fact that patients who meet the study criteria may be "imaged" infrequently, and the imaging technologist (MR or CT) may not remember or may not perform the study in the exact manner prescribed by the clinical imaging protocol. In addition, since there is no "on-line" method of transmitting the acquired image data to the CRO, the Imaging Center must store the image data on one or more pieces of removable media (CD or DVD) and then ship the media to the CRO via conventional ground or air transportation. These additional steps take invaluable time away from the technologist thereby reducing his/her productivity. They also introduce latency in the process because of the extra effort required to ship the data to the CRO. These sources of error cause the Sponsor to incur unnecessary expenses.

Figure 2:
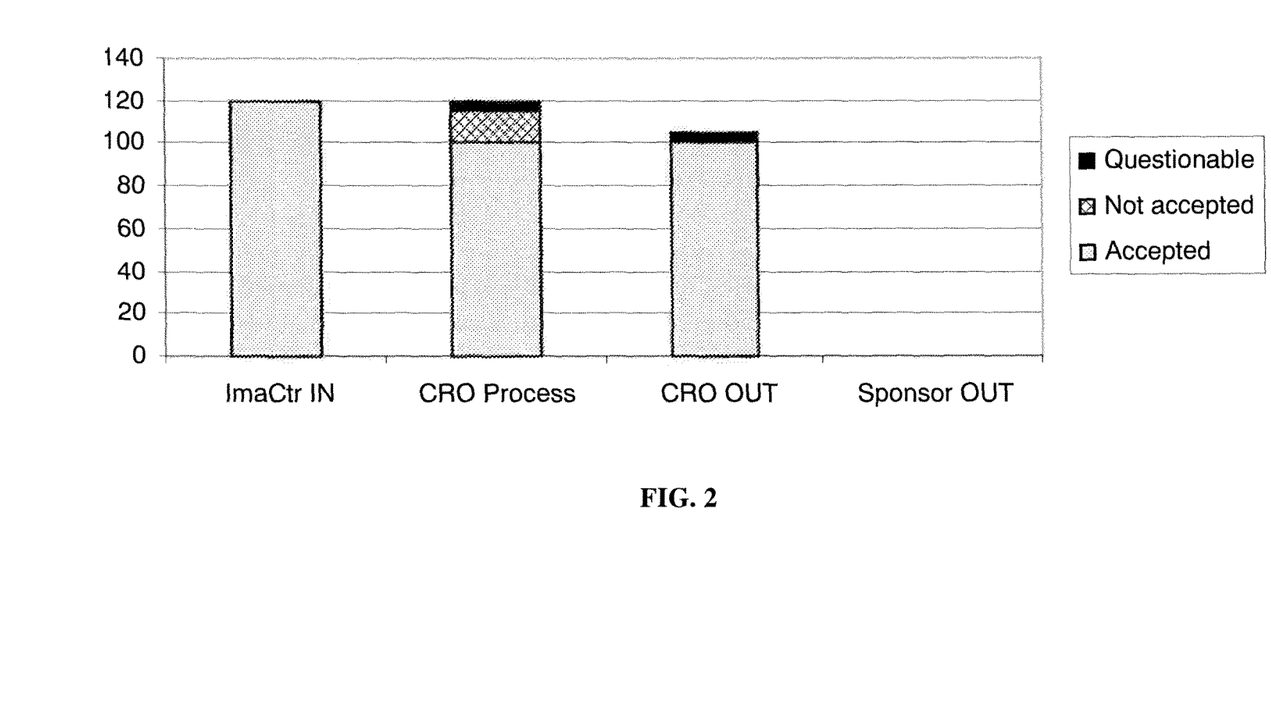
FIG. 2 shows a relationship between the total number of medical images acquired as part of a clinical trial program, and the number of those images that are useable as part of the program.

FIG. 2 is an illustration of the number of studies at each step in an exemplary conventional process. As can be seen, for 120 images sent to the CRO by the Imaging Center, only 100 are accepted, 15 are rejected, and 5 partially qualify. Thus, of the original 120 images, only 105 are ultimately used by the CRO in generating the final report to the Sponsor.

Figure 3:
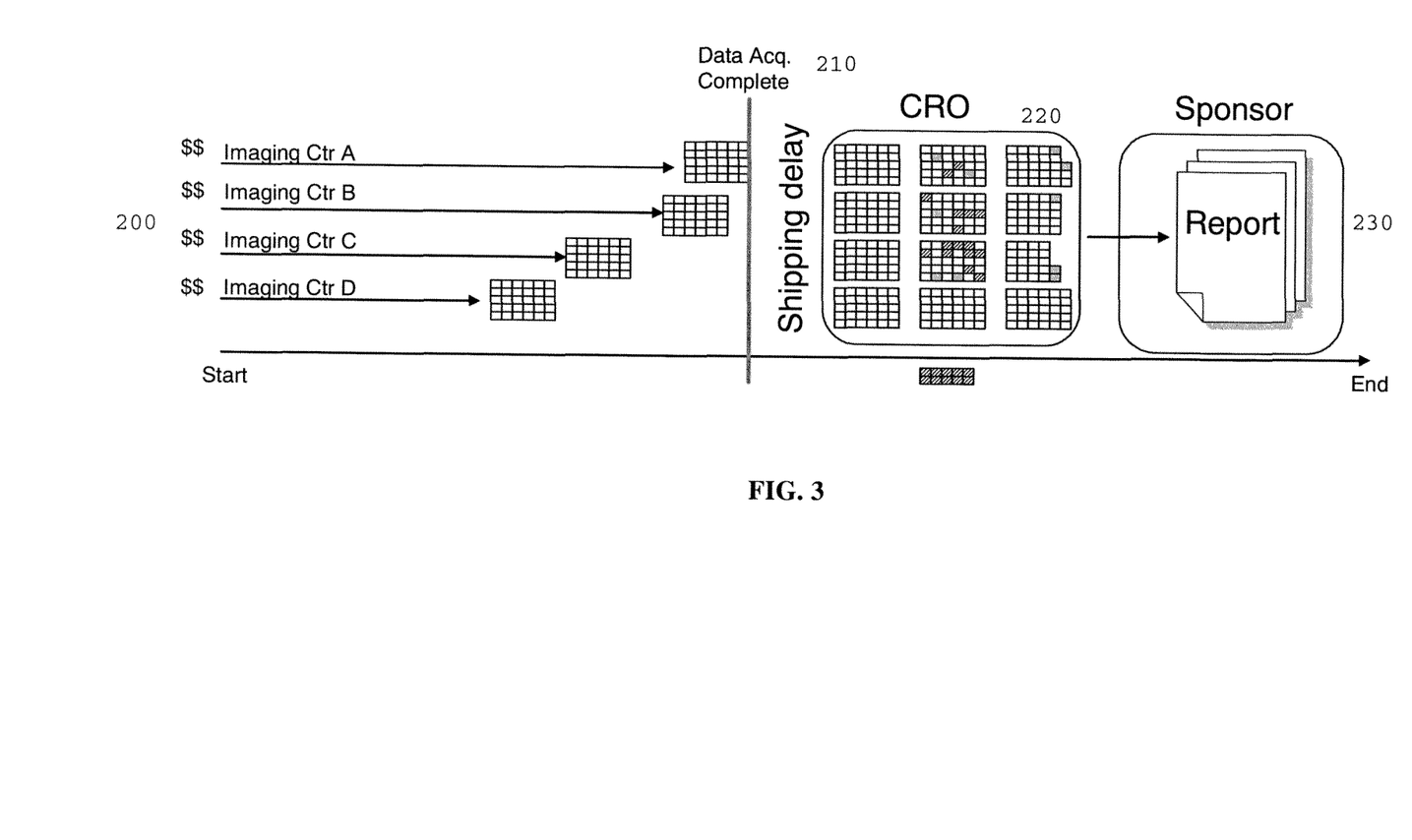
FIG. 3 shows the data flow in a typical clinical trial process resulting in a final report with no images.

FIG. 3 illustrates the data flow in a typical clinical trial, in which multiple imaging centers (Imaging Ctrs. A-D) provide image data to a CRO for analysis, compilation and transmittal of a final report to the Sponsor. At step 200, each imaging center (A-D) is typically contracted by the Sponsor for a fixed dollar amount to provide a fixed number of "studies" (i.e., patient images). The number contracted for is usually somewhat larger than what is required for the actual study to take into account the common existence of "unusable" studies (i.e., those that fail to comply with the study protocol for any of a variety of reasons). Once the CRO receives the studies at step 210 (Data Acq. Complete"), it analyzes the studies to verify their compliance to the study protocol.

As noted, it is often the case that a number of studies do not comply (in FIG. 3, non-compliant studies out of the total group of studies 220 received by the CRO are marked with a hash box). These studies must be removed from the data pool and are not used in formulating the report (shown below the timeline). Some studies may also partially qualify (marked in dark gray in the figure) and will be forwarded to the Sponsor. For non-compliant studies, or for partially qualifying studies, it is not practical to re-scan the patient because the patient will have long since left the Imaging Center (since imaging may occur days or weeks before the images are reviewed by the CRO). Furthermore, since the CRO determines whether a study qualifies to be included, and the Imaging Center may not receive any feedback as to why the study was rejected, the Imaging Center has no means of rapidly improving their process in order to achieve a higher success rate. If the quality determination was done at the Imaging Center, it would have the opportunity to do a root cause analysis and implement process improvements that would increase their success. The Sponsor considers the report(s) received from the CRO at 230 to make final judgments about the experiment. Currently images are not available to the Sponsor to corroborate the findings. The timeline ends when the final study report is produced by the Sponsor.

The existing practice is unnecessarily slow and inefficient, and the mechanics of shipping the data on removable media is slow and cumbersome. In addition to the delay, there are substantial costs involved in packaging and postage for the data media (CDs, DVDs)). Furthermore, the infrequency of qualified patients is a root cause for many errors. The business model of paying for a fixed number of studies, even though much of the data may not be useable, is non-optimal.

Thus, there is a need for a system that will speed the process of obtaining and reviewing medical images acquired as part of a clinical trials program. Such a system should minimize the number of unusable images, thus reducing overall costs borne by the trial Sponsor.

SUMMARY OF THE DISCLOSURE

A method is disclosed for contracting with imaging centers for the provision of medical images as part of a clinical trials process, comprising: providing a study protocol as part of a clinical trials process, the study protocol including a medical imaging protocol, the study protocol or the medical imaging protocol including a requirement for obtaining a predetermined quantity of patient medical images according to a minimum acceptance standard; contracting with a plurality of imaging centers to provide patient medical images according to the medical imaging protocol; and accepting patient medical images from said plurality of imaging centers on a first-come, first-served basis, until a total number of medical images accepted equals the predetermined quantity, and refusing acceptance of further patient medical images from said plurality of imaging centers.

Also disclosed is a machine readable storage device tangibly embodying a series of instructions executable by the machine to perform a series of steps, the steps comprising: providing a study protocol as part of a clinical trials process, the study protocol including a medical imaging protocol, the study protocol or the medical imaging protocol including a requirement for obtaining a predetermined quantity of patient medical images according to a minimum acceptance standard; contracting with a plurality of imaging centers to provide patient medical images according to the medical imaging protocol; accepting patient medical images from said plurality of imaging centers on a first-come, first-served basis, until a total number of medical images accepted equals the predetermined quantity, and refusing acceptance of further patient medical images from said plurality of imaging centers.

Further disclosed is a system for contracting with imaging centers for the provision of medical images as part of a clinical trials process, comprising: means for providing a study protocol as part of a clinical trials process, the study protocol including a medical imaging protocol, the study protocol or the medical imaging protocol including a requirement for obtaining a predetermined quantity of patient medical images according to a minimum acceptance standard; means for contracting with a plurality of imaging centers to provide patient medical images according to the medical imaging protocol; and means for accepting patient medical images from said plurality of imaging centers on a first-come, first-served basis, until a total number of medical images accepted equals the predetermined quantity, and refusing acceptance of further patient medical images from said plurality of imaging centers.

BRIEF DESCRIPTION OF THE DRAWINGS

The accompanying drawings illustrate preferred embodiments of the disclosure so far devised for the practical application of the principles thereof, and in which.

DETAILED DESCRIPTION OF THE DISCLOSURE

This disclosure outlines a process by which trial Sponsors/CROs can more rapidly acquire high quality images required to complete a study protocol as part of a clinical trials process, thereby reducing overall cost, reducing the time required to complete the study, and reducing the "waste" of receiving images that are not fit for use in the study. This enhancement provides a new business model in which study Sponsors reimburse imaging centers only for those studies that fulfill experimental protocol parameters, and facilitates an open and competitive market where many imaging centers can compete for reimbursement by being the first to send qualified data sets to the Sponsor and/or CRO.

Figure 4:
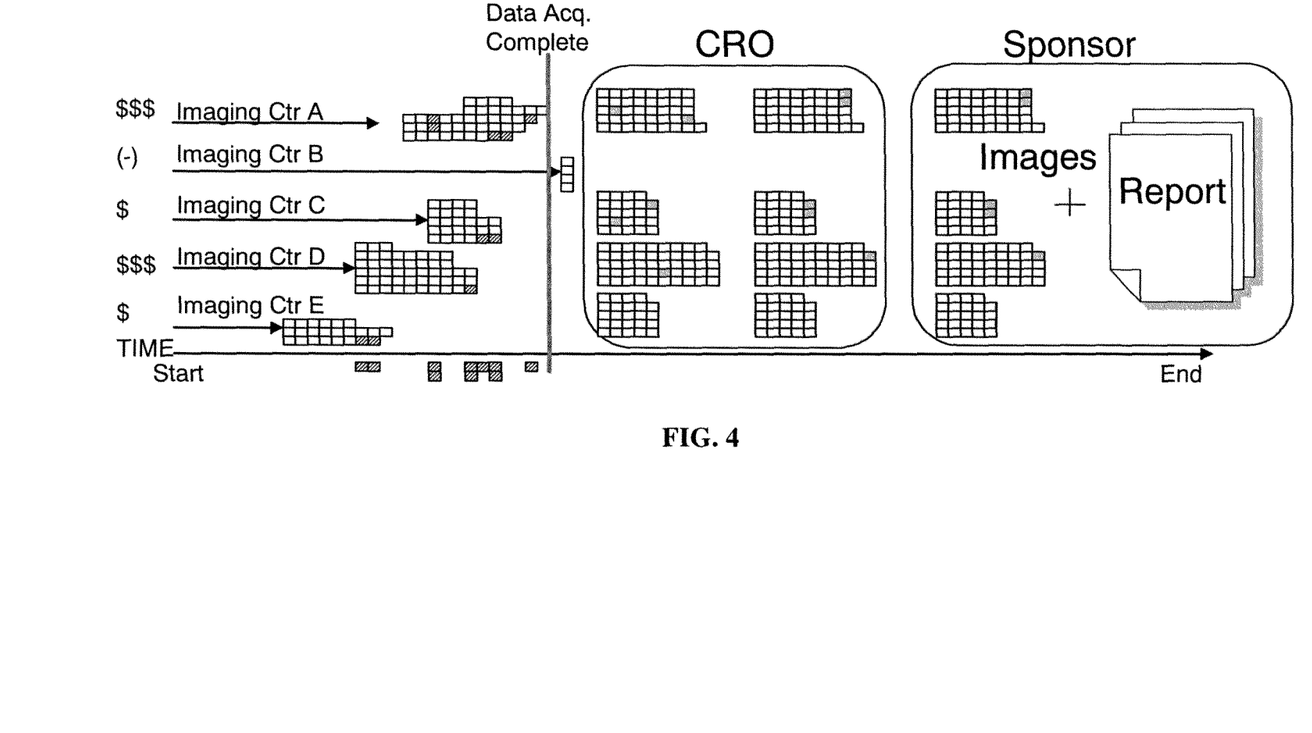
FIG. 4 shows the disclosed system in which a plurality of imaging centers compete to provide medical images in addition to the final report as part of a clinical trial.

Referring now to FIG. 4, an improved system and method of obtaining medical image data from a plurality of imaging centers will be described. In general, the system and method introduces an element of competition between imaging centers in order to obtain the best quality images, in less time than with the previous process. To implement this competitive element, the agreements between the Sponsor and the Imaging Centers may stipulate that the Sponsor is only required to accept a certain total number of medical images (e.g., the total number of images required to support the clinical trial according to the clinical protocol), and is free to reject any medical images that either do not comply with the protocol, or which exceed the total number of medical images required for the study. This is contrary to the prior method in which the Sponsor contracts with a plurality of Imaging Centers to have each submit a fixed number of studies.

As shown in FIG. 4 illustrates the main advantages of the disclosed system and method. The time to complete the data acquisition ("Data Acq. Complete") is shorter because of the competitive situation between the Imaging Centers. Thus, qualifying studies are accepted from the Imaging Centers (and compensated for) on a first-come, first served, basis. In this illustration, Imaging Centers A, B, C, D & E represent Imaging Centers with which the Sponsor has contracted to provide medical images in support of a clinical trial. In practice, any number of Imaging Centers may be utilized.

As can be seen, Imaging Centers A and D receive the most money from the Sponsor (represented in the figure by dollar signs ($$$)) of the five Imaging Centers because they submitted more studies to the CRO that fulfill the study criteria (signified by light grey boxes), in a shorter period of time, than Imaging Centers B, C and E. Imaging Centers C & E received less money ($) from the Sponsor because they submitted fewer studies to the CRO that fulfill the study criteria, and their submissions were later than the submissions of Imaging Centers A & D. Imaging Center B failed to receive any money because, although it submitted four studies of sufficient quality, the total number of medical images required for the study had already been received from the other Imaging Centers.

In this manner, the Sponsor pays only for those studies that meet the clinical protocol. As can be seen, unacceptable studies are shown below the time line in the figure as the hash-marked boxes. According to the disclosed system and method, the CRO would not even receive or accept these studies, and thus the Sponsor would not have to pay for them. With the disclosed system and method, each of the Imaging Centers is highly motivated to: (a) provide only studies that comply with the medical imaging protocol, and (b) provide them quickly to ensure that they get paid for the studies they submit.

The disclosed system and method also provides a mechanism for performing quality checks at the Imaging Centers. If studies fail the quality check (illustrated as hash marked boxes), they are not permitted to be transmitted to the CRO for analysis. In this manner, the CRO only receives pre-qualified data, thereby providing operational efficiencies. In one embodiment, this quality checking mechanism is immediate, and may occur while the patient is still at the Imaging Center. This provides the Imaging Center with the opportunity to immediately re-scan the patient in the event that the data do not fulfill study criteria. As previously noted, with prior techniques these quality checks were performed later by the CRO, and thus there was no practical opportunity to properly re-scan the patient.

With the disclosed system and method, although non-compliant image data are immediately rejected, partially-qualified data (illustrated as dark grey boxes in the CRO block) may still be sent to the CRO for consideration. The Imaging Center will receive payment for these partially-qualifying images, although perhaps at a lower rate than or fully qualifying data. These partially qualified data will be passed to the Sponsor for final consideration and potential inclusion in the final Report.

In order to implement the system and method, the Sponsor will make available to Imaging Centers and CROs an IT solution that performs the previously-noted quality checks on the image data sets. The IT solution may also be used to rapidly transmit the qualifying image data (and in some cases the partially-qualifying image data) to the CRO and Sponsor via an interface, such as a public or private network, one non-limiting example of which being the Internet. Examples of appropriate equipment used for collecting and transmitting the medical image data may be the same or similar to that described in pending U.S. Patent Application Publication 2005/0251011 to Zahlmann et al., titled "Clinical Trial Image and Data Processing System," and U.S. Patent Application Publication 2007/0150223 to Abraham-Fuchs et al., titled "Method for Verifying Compliance with a Performance Specification Assigned to a Medical Working Practice," the entirety of which applications are incorporated by reference herein.

Thus, at the beginning of the study the Sponsor makes known to potential Imaging Centers what image data sets will be required along with the clinical protocol that must be followed. The Sponsor may verify the readiness of each of the Imaging Centers before that Center is qualified to participate. Once qualified, the Imaging Centers should find patients that fulfill the study requirements and use the disclosed system and method to rapidly send the studies to the CRO and Sponsor for consideration.

If the transmitted studies fulfill the trial protocol, and if more studies are still required to complete the clinical trial, then the image data set is accepted by the CRO and the Imaging Center is reimbursed for the study. If, however, the study fulfills the trial protocol but the Sponsor already has sufficient data to complete the trial, no payment is made to the Imaging Center. As will be appreciated, this system and method provides strong incentives to the Imaging Centers to provide high quality (i.e., compliant) studies to the CRO and Sponsor in as fast and efficient manner possible to ensure that the Imaging Center receives payment for its studies. This benefits the CRO and Sponsor because they receive studies faster due to the electronic methods of data transmission and the competition between Imaging Centers to provide qualifying studies. It also benefits the Imaging Center since they will not lose productivity creating and shipping CDs that ultimately will not be used.

It will be appreciated that the determination as to whether a particular study is "qualifying" or "partially qualifying" can be made by the CRO or Sponsor, or it can be made at the Imaging Center. Additionally, the system and method can be used to provide medical images from a plurality of Imaging Centers to a plurality of CROs, as part of a single or multiple clinical trials.

It will also be appreciated that the disclosed method may be extended to applications such as patient safety monitoring during clinical trials, and patient safety monitoring for other diseases. Qualified personnel at the Sponsor site (i.e. trained radiologist or scientist) may be familiar with suspected side effects of certain compounds being studied because of his/her exposure to a large number of images of this exact patient population. For example, a compound that is a candidate drug to treat one disease may have the unwanted potential side effect of causing hemorrhage in surrounding blood vessels. By viewing T2* MRI images one may appreciate subtle symptoms of this side effect early on and thus have the opportunity to take actions that would improve patient safety. This observation may not be apparent to the staff at the Imaging Center or CRO since they may not be aware of all potential side effects. Even if they are aware they may not be skilled in observing the symptom because of the relatively few studies that they are exposed to. The Sponsor on the other hand has the benefit of reviewing many images from many sites and therefore has a greater probability of observing the symptom.

As noted, use of the disclosed method enables Sponsors of clinical trials only pay for data sets that fulfill the study criteria, resulting in cost reductions for the Sponsor. The method also enables earlier completion of the clinical trial process because an open and competitive market is established between Imaging Centers whose goals are to collect revenue by participating in the process, one criteria of which is the timely transmission of high-quality studies. Instead of a fixed fee for a specified number of studies, the Sponsor can pay Imaging Centers only for studies that fulfill the study criteria. Ultimately Sponsors will only pay those Imaging Centers that provide high quality data in a timely manner. In addition, the Sponsors will not have to pay CROs additional fees for analyzing studies that do not comply with the clinical and/or medical imaging protocol.

The method also enables the Sponsor to check the timeliness of processing performed by the CROs. Thus, the Sponsor may establish variable based compensation of CROs based on the timeliness and quality of their analysis.

The method may also result in a reduction in a total time required to complete a particular clinical trial because data sets are electronically transported to the CRO and Sponsor, thus eliminating shipping and packaging costs associated with prior methods. Additionally, because the system and method enables the Sponsor to know the exact status of how many valid data sets have been successfully acquired, the Sponsor can stop the data acquisition phase of the trial sooner, thus saves money and shortening the duration of the trial.

The system and method may also improve safety of the image acquisition process. For example, if the Sponsor learns of a safety related patient issue (e.g., an adverse reaction or condition) based on the rapid transmission and review of a particular medical image, the Sponsor may be able to react in a more timely fashion during clinical trial. Currently such notification may come through various other means such as an electronic data capture (EDC) system, but such processes are much slower than those possible with the present disclosure.

In addition, the disclosed system and method enables performing initial quality checks at the time of data acquisition for each patient. When the quality check performed at the Imaging Center immediately after a scan identifies a deficiency, the scan may be repeated because the patient is still available at the scanner. The "near-real" time quality check of the data enables repeat scans when necessary. Being able to re-scan a patient may shorten the duration of a clinical trial because it avoids the delays that can be incurred while waiting for another patient who fulfills the study criteria. The audit trail for the data elements would also begin earlier—at the Imaging Center—instead of the current processes in which the data audit trail begins when the CDs containing the image data are received by the CRO.

The disclosed system and method also may reduce total costs by eliminating the need for CRO to de-identify the data sets and manage the study identifiers, since the system and method automatically provides this function.

The system and method enables Imaging Centers to improve their quality and performance because errors in data will be detected immediately at the imaging site. Imaging Centers will have reduced costs because it will no longer be necessary to spend time creating CDs and DVDs containing the image data and shipping them to the CRO, thus eliminating the unproductive labor time as well as charges associated with packaging and shipping. Additionally, providing the ability to re-scan a patient (when quality parameters are not fulfilled) enhances Imaging Center efficiencies by eliminating the current wait associated with finding another patient from whom a qualified data set may be produced.

The system and technique described herein may be automated by, for example, tangibly embodying a program of instructions upon a computer readable storage media, capable of being read by machine capable of executing the instructions. A general purpose computer is one example of such a machine. Examples of appropriate storage media are well known in the art and would include such devices as a readable or writeable CD, flash memory chips (e.g., thumb drive), various magnetic storage media, and the like.

Figure 5:
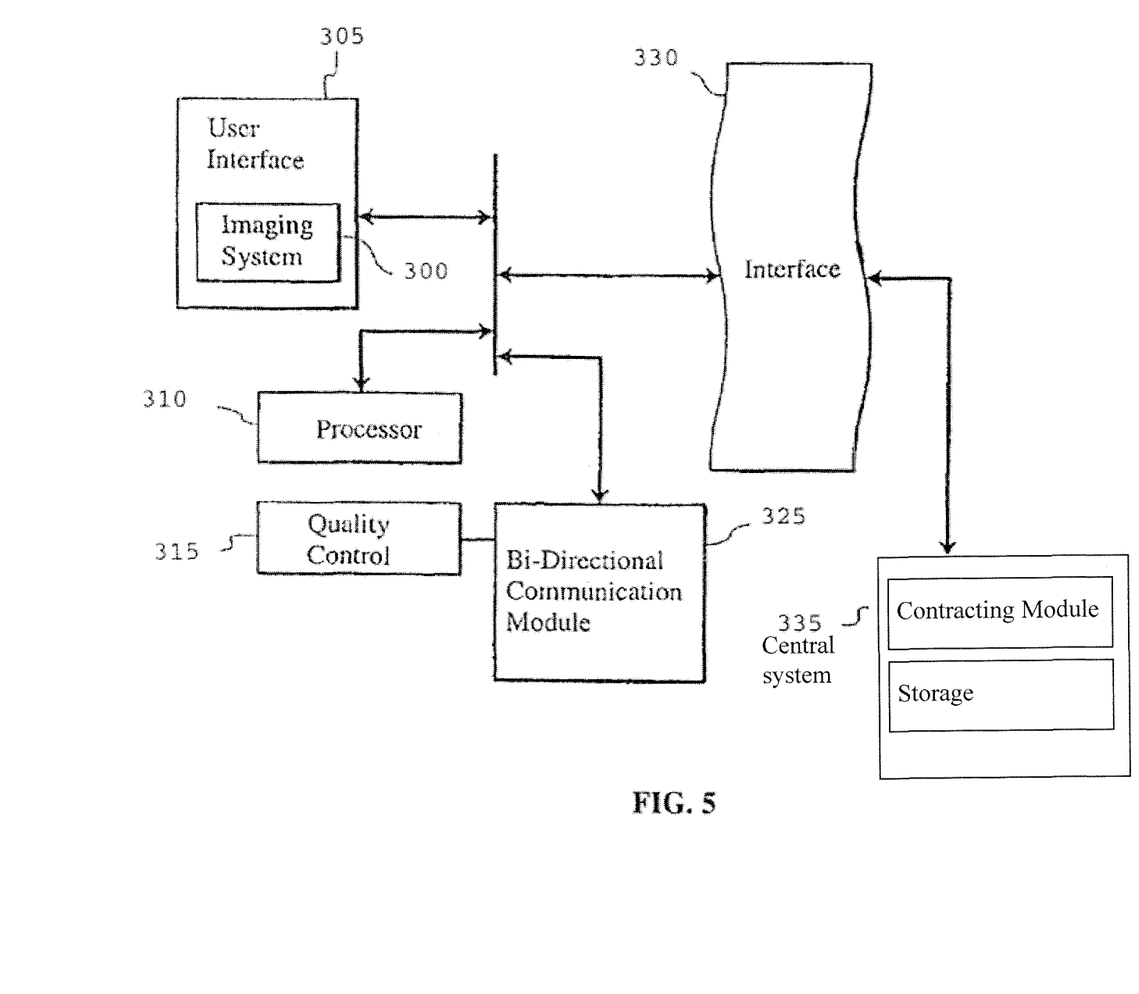
FIG. 5 shows a system for supporting a clinical trial involving the acquisition and transmission of image data.

An exemplary clinical trial system, for implementing the disclosed method, is shown in FIG. 5, and includes modules 300-135 that provide a comprehensive clinical trial infrastructure and process framework. In the system, imaging modality 300, located at a trial site, acquires medical images. User interface (UI) 305 facilitates use of imaging system 300 for clinical studies (not just for conventional clinical routine) and may ensure use of a consistent set of parameters enabling comparability of the images within a clinical study. User interface 305 initiates generation of data representing a composite display image that includes image elements for initiating different functions supporting a clinical trial in response to user activation. Such functions include generating (by using processor 310) and displaying patient non-specific medical image representative data from patient specific medical image representative data.

Processor 310 renders patient medical data (including medical image data) anonymous, verifies identity and security of users and information sources and supports identification of users and information sources at a particular trial site. Unit 315 provides additional functions including a quality control processor. The quality control processor ensures quality of clinical images and adherence to the clinical trail protocol or medical imaging protocol, for example. For this purpose, the quality control processor in unit 115 monitors image quality, the degree of compliance with predetermined standards and the degree of compliance with predetermined procedures. Further, the quality control processor, in response to a determined deficiency at least one of, initiates generation of an alert message to a user and initiates remedial action to correct the determined deficiency.

Unit 325 includes a bidirectional communication function for transferring and communicating processed data via interface 330 to a central system 335 supporting clinical trial management by a CRO, or trial Sponsor, for example.

Bidirectional interface 330 enables a trial Sponsor or CRO employing central system 335 to select characteristics and requirements that determine operation of quality control functions within the system and also to determine operational functions of user interface 305 of imaging system 100. Interface 330 also enables a trial sponsor to configure interface 330 to receive data in a selected predetermined format. Interface 330 is a flexible, common interface that connects an image source (e.g., imaging system 300) in an image based clinical trial (such as performed by a healthcare provider) and a sponsor or trial manager. Central system 335 may include a clinical trial PACS (Picture Archiving and Communication System) and incorporates a Radiology Information System (RIS) and collates and integrates images from systems of different vendors.

The features of the system and technique have been disclosed, and further variations will be apparent to persons skilled in the art. All such variations are considered to be within the scope of the appended claims. Reference should be made to the appended claims, rather than the foregoing specification, as indicating the true scope of the subject system and technique.

What is claimed is:

1. A system, including a processor, for contracting with imaging centers for the provision of patient medical images as part of a clinical trials process, comprising:

means for providing a study protocol as part of a clinical trials process, the study protocol including a medical imaging protocol, the study protocol or the medical imaging protocol including a requirement for obtaining a predetermined quantity of patient medical images according to a minimum acceptance standard;

means for contracting with a plurality of imaging centers to provide patient medical images according to the medical imaging protocol; and means for accepting patient medical images from one or more of said plurality of contracted imaging centers, wherein the means for accepting patient medical images is configured to implement competition among the plurality of contracted imaging centers by:

accepting patient medical images from one or more of the plurality of contracted imaging centers on a first-come, first-served basis, until it is determined based on a comparison that a total number of accepted patient medical images that meet the minimum acceptance standard equals the predetermined quantity, and automatically refusing acceptance of further patient medical images from said plurality of contracted imaging centers after the total number of accepted patient medical images that meet the minimum acceptance standard equals the predetermined quantity, wherein the quality of the patient medical images is determined by a quality control processor.

2. The system of claim 1, wherein the means for accepting patient medical images from said plurality of contracted imaging centers accepts said patient medical images in electronic form transmitted from said contracted imaging centers via an interface.

3. The system of claim 1, further comprising means for compensating the contracted imaging centers only for the accepted patient medical images.

4. The system of claim 1, further comprising means for rejecting patient medical images that do not meet the minimum acceptance standard.

5. The system of claim 1, further comprising means for performing an initial quality check of the patient medical images from at least one of the plurality of contracted imaging centers and transmitting only those patient medical images that meet the minimum acceptance standard.

6. The system of claim 1, further comprising:

means for contracting with a clinical research organization (CRO) to analyze the accepted patient medical images and incorporate the analysis into a report, wherein the CRO is compensated for the analysis and the report according to a variable scale based on at least one of a timeliness criteria of the analysis and the report and a quality criteria of the analysis and the report.

7. A computer system for contracting with imaging centers for the provision of patient medical images as part of a clinical trials process, comprising:

a communications interface for electronically communicating; and a plurality of computer processors configured to perform actions, including:

communicating with a central system having a processor to receive a minimum acceptance standard, wherein the central system includes a radiology information system;

utilizing at least one computer processor, wherein the at least one computer processor is associated with a clinical research organization (CRO), to provide a study protocol as part of a clinical trials process, the study protocol including a medical imaging protocol, the study protocol or the medical imaging protocol including a requirement for obtaining a predetermined quantity of patient medical images according to the minimum acceptance standard;

contracting with a plurality of imaging centers to provide patient medical images according to the medical imaging protocol; and accepting, by the clinical research organization (CRO), patient medical images from one or more of said plurality of contracting imaging centers so as to implement competition among the plurality of contracted imaging centers by:

accepting patient medical images from one or more of the plurality of contracted imaging centers on a first-come, first-served basis, until it is determined based on a comparison that a total number of accepted patient medical images that meet the minimum acceptance standard equals the predetermined quantity, and automatically refusing acceptance of further patient medical images from said plurality of contracted imaging centers after the total number of accepted patient medical images that meet the minimum acceptance standard equals the predetermined quantity, wherein the quality of the patient medical images is determined by a quality control processor.

8. The computer system of claim 7, wherein the step of accepting patient medical images from said plurality of contracting imaging centers comprises accepting said patient medical images in electronic form transmitted from said contracted imaging centers via an interface.

9. The computer system of claim 7, further comprising compensating the contracted imaging centers only for the accepted patient medical images.

10. The computer system of claim 7, further comprising rejecting patient medical images transmitted from said contracted imaging centers that do not meet the minimum acceptance standard.

11. The computer system of claim 7, further comprising performing an initial quality check of the patient medical images from at least one of the plurality of contracted imaging centers and transmitting only those patient medical images that meet the minimum acceptance standard.

12. The computer system of claim 10, further comprising not compensating the contracted imaging centers for the rejected patient medical images.

13. The computer system of claim 7, further comprising contracting with the clinical research organization (CRO) to analyze the accepted patient medical images and incorporate the analysis into a report, wherein the CRO is compensated for the analysis and the report according to a variable scale based on at least one of a timeliness criteria of the analysis and the report and a quality criteria of the analysis and the report.

14. A non-transitory storage device tangibly embodying a series of instructions and configured to, when executed by a processor, perform a series of steps, the steps comprising:

providing a study protocol as part of a clinical trials process, the study protocol including a medical imaging protocol, the study protocol or the medical imaging protocol including a requirement for obtaining a predetermined quantity of patient medical images according to a minimum acceptance standard;

contracting with a plurality of imaging centers to provide patient medical images according to the medical imaging protocol; and accepting patient medical images from one or more of said plurality of contracted imaging centers so as to implement competition among the plurality of contracted imaging centers by:

accepting patient medical images from one or more of the plurality of contracted imaging centers on a first-come, first-served basis, until it is determined based on a comparison that a total number of accepted patient medical images that meet the minimum acceptance standard equals the predetermined quantity, and automatically refusing acceptance of further patient medical images from said plurality of contracted imaging centers after the total number of accepted patient medical images that meet the minimum acceptance standard equals the predetermined quantity, wherein the quality of the patient medical images is determined by a quality control processor.

15. The storage device of claim 14, wherein the step of accepting patient medical images from said plurality of contracted imaging centers comprises accepting said patient medical images in electronic form transmitted from said contracted imaging centers via an interface.

16. The storage device of claim 14, further comprising compensating the contracted imaging centers only for the accepted patient medical images.

17. The storage device of claim 14, the steps further comprising rejecting patient medical images transmitted by from said contracted imaging centers that do not meet the minimum acceptance standard.

18. The storage device of claim 14, the steps further comprising performing an initial quality check of the patient medical images from at least one of the plurality of contracted imaging centers and transmitting only those patient medical images that meet the minimum acceptance standard.

19. The storage device of claim 17, the steps further comprising not compensating the contracted imaging centers for the rejected patient medical images.

20. The storage device of claim 14, the steps further comprising:

contracting with a clinical research organization (CRO) to analyze the accepted patient medical images and incorporate the analysis into a report, wherein the CRO is compensated for the analysis and the report according to a variable scale based on at least one of a timeliness criteria of the analysis and the report and a quality criteria of the analysis and the report.

* * * * *